(12) United States Patent
Takekoshi

(10) Patent No.: US 6,469,205 B1
(45) Date of Patent: Oct. 22, 2002

(54) METHOD FOR OXIDATION OF XYLENE DERIVATIVES

(75) Inventor: Tohru Takekoshi, Scotia, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/681,007

(22) Filed: Nov. 14, 2000

Related U.S. Application Data

(60) Provisional application No. 60/166,970, filed on Nov. 23, 1999.

(51) Int. Cl.$^7$ .................. C07C 51/16; C07C 51/255; C07C 65/00
(52) U.S. Cl. .................. 562/412; 562/422; 562/888
(58) Field of Search .................. 562/412, 888, 562/422

(56) References Cited

U.S. PATENT DOCUMENTS

| | | | |
|---|---|---|---|
| 3,402,184 A | | 9/1968 | Berthoux et al. ......... 260/346.4 |
| 4,034,007 A | * | 7/1977 | Gottesman .................. 260/524 |
| 4,215,053 A | | 7/1980 | Palmer et al. ........... 260/346.7 |
| 4,299,977 A | | 11/1981 | Kuhlmann et al. ......... 562/416 |
| 4,322,549 A | | 3/1982 | Kuhlmann et al. ......... 562/416 |
| 4,387,243 A | | 6/1983 | Naim et al. ................. 562/413 |
| 5,225,573 A | | 7/1993 | Shorr et al. ................. 549/246 |
| 5,322,954 A | | 6/1994 | Seper et al. | |

FOREIGN PATENT DOCUMENTS

| | | | |
|---|---|---|---|
| DE | 22 36 875 | * | 3/1974 |
| GB | 856 245 | | 12/1957 |
| JP | 02-129143 | | 5/1990 |
| JP | 07-258152 | | 10/1995 |

OTHER PUBLICATIONS

International Search Report for International Application No. PCT/US 00/31719.

Naum Glukhovskii et al.: "Preparation of 4–Bromophthalic Anhydride By Oxidation of 4–Bromo–Ortho–Zylene", Journal of Chemical Technology and Biotechnology, vol. 63, No. 2, Jun. 1, 1995.

Nazarenko et al.: "Preparation of Monochlorophthalic Acids By the Liquid Phase . . .", UKR.KHIM:ZH., vol. 50, No. 6, pp. 644–647, Chemical Abstracts, vol. 101, No. 25, Dec. 17, 1984.

\* cited by examiner

Primary Examiner—Mukund J. Shah
Assistant Examiner—Zachary C. Tucker
(74) Attorney, Agent, or Firm—S. Bruce Brown; Noreen C. Johnson

(57) ABSTRACT

Xylene derivatives, such as chloro-ortho-xylene, are oxidized in the absence of solvent or added promoter in the presence of at least one metal catalyst. The primary products are chlorophthalic anhydride and chlorotoluic acid.

18 Claims, No Drawings

METHOD FOR OXIDATION OF XYLENE DERIVATIVES

CROSS REFERENCE TO RELATED APPLICATIONS

This application claims priority of a Provisional Application entitled "Method for Oxidation of Xylene Derivatives" by Tohru Takekoshi, Ser. No. 60/166,970 and filed Nov. 23, 1999.

BACKGROUND OF INVENTION

This invention relates to a method for oxidizing xylene derivatives. More particularly, the invention relates to a method for oxidizing a substrate comprising at least one halo-ortho-xylene in the presence of at least one metal catalyst and in the absence of solvent or added promoter to provide a product comprising halo-phthalic anhydride. In one key embodiment the invention relates to a method for producing a product comprising 4-chlorophthalic anhydride.

Methods for oxidizing ortho-xylene are known. Most of these methods either require the presence of a corrosive solvent such as acetic acid or the presence of a promoter or both. For example, U.S. Pat. No. 3,402,184 describes oxidation of ortho-xylene in acetic acid solvent in the presence of a bromine promoter. U.S. Pat. Nos. 4,215,053, 4,299,977, 4,322,549, and 4,387,243 describe oxidation of ortho-xylene in the absence of solvent but in the presence of a bromine promoter. Methods for preparing 4-chlorophthalic anhydride are also known. However, these methods typically involve aromatization of a Diels-Alder adduct of chloroprene and a maleic anhydride as in U.S. Pat. No. 5,322,954, or chlorination of phthalic acid as in Japanese patent applications 07258152 and 02129143. The latter chlorination process may produce polychlorinated biphenyls (PCBs).

There is a need, therefore, to provide a method for oxidizing a substrate comprising a halo-ortho-xylene which does not require a solvent or added promoter, particularly a corrosive solvent or promoter. There is also a need for a method for producing 4-chlorophthalic anhydride which does not involve handling toxic chloroprene or chlorine gas, and which does not produce PCBs.

SUMMARY OF INVENTION

In one embodiment the invention is a method for oxidizing a substrate comprising at least one halo-ortho-xylene which comprises combining the substrate in the absence of solvent or added promoter with at least one metal catalyst and heating in the presence of an oxygen source.

In another embodiment the invention is a method for oxidizing a substrate comprising 4-chloro-ortho-xylene which comprises combining chloro-ortho-xylene in the absence of solvent or added promoter with at least one metal catalyst which is a metal compound with a metal selected from the group consisting of cobalt, manganese, vanadium, copper, molybdenum, and iron, and heating in the presence of molecular oxygen to produce a product mixture comprising 4-chlorophthalic anhydride and chlorotoluic acid.

In still another embodiment the invention is a method for producing 4-chlorophthalic anhydride which comprises oxidizing a substrate comprising 4-chloro-ortho-xylene, optionally in the presence of chlorotoluic acid, which comprises the steps of (i) combining substrate in the absence of solvent or added promoter with at least one metal catalyst which is a metal compound with a metal selected from the group consisting of cobalt, manganese, vanadium, copper, molybdenum, and iron, and heating in the presence of molecular oxygen to a temperature in a range of between about 100° C. and about 230° C. at atmospheric pressure, wherein the molar ratio of substrate to the at least one metal catalyst is in a range of about 80–180:1; and (ii) isolating product comprising 4-chlorophthalic anhydride.

DETAILED DESCRIPTION

In one embodiment the substrate comprising at least one halo-ortho-xylene of the present invention preferably comprises a monohalo-ortho-xylene, more preferably 4-halo-ortho-xylene, most preferably 4-fluoro- or 4-chloro-ortho-xylene. In another embodiment the substrate comprises a mixture of 4-halo- and 3-halo-ortho-xylene, preferably a mixture of 4-fluoro- and 3-fluoro-ortho-xylene or a mixture of 4-chloro- and 3-chloro-ortho-xylene. When 3-halo-ortho-xylene is present, it comprises about 0.001–15 molar percent, preferably about 0.01–12 molar percent, and more preferably about 0.1–10 molar percent of total substrate.

In yet another embodiment the substrate comprises at least one halo-ortho-xylene as described above, optionally in the presence of at least one halotoluic acid, preferably at least one chlorotoluic acid (also known as chloro methylbenzoic acid), more preferably either (a) 4-chloro-2-methyl benzoic acid or (b) 5-chloro-2-methylbenzoic acid or (c) a mixture thereof, and still more preferably a mixture of either or both of (a) and (b) with either (d) 4-halo-ortho-xylene, or (e) a mixture of 4-halo- and 3-halo-ortho-xylene. Halo-toluic acid may be either added to the substrate or may be present as a consequence of partial oxidation of halo-ortho-xylene. As a consequence of partial oxidation the amount of halo-toluic acid in the substrate will vary with such factors as reaction temperature, time, and catalyst.

In still another embodiment the substrate comprises a mixture of ortho-xylene either with (d) 4-halo-ortho-xylene, or with (e) a mixture of 4-halo- and 3-halo-ortho-xylene, or with at least one chlorotoluic acid, or with a mixture of chlorotoluic acid with either (d) 4-halo-ortho-xylene, or (e) a mixture of 4-halo-and 3-halo-ortho-xylene. When ortho-xylene is present, it comprises about 0.001–10 molar percent and preferably about 0.01–1 molar percent of total substrate. An especially preferred substrate comprises 4-chloro-ortho-xylene, optionally in combination with at least one of 3-chloro-ortho-xylene, ortho-xylene, or chlorotoluic acid.

At least one metal catalyst is used in the present invention. The at least one metal catalyst comprises a metal compound with a metal selected from the group consisting of cobalt, manganese, vanadium, copper, molybdenum, and iron, and mixtures thereof. Preferably, a metal compound is a salt of the metal and more preferably an acetate or acetylacetonate of the metal. Illustrative metal compounds which are suitable for use in the invention include cobalt (II) acetate, manganese (II) acetate, vanadyl (IV) acetate (VO[OC(O)CH$_3$]$_2$), vanadyl (IV) acetylacetonate, copper (I) acetate, molybdenyl (VI) acetylacetonate (MoO$_2$[C$_5$H$_7$O$_2$]), iron (II) acetate, and mixtures thereof. The molar ratio of halo-ortho-xylene substrate to the at least one metal catalyst is in a range of about 20–500:1, preferably in a range of about 50–250:1, and most preferably in a range of about 80–180:1. In especially preferred embodiments the molar ratio of halo-ortho-xylene substrate to the at least one metal catalyst is about 100:1. The at least one metal catalyst may be added in one portion to the substrate or in more than one portion during the course of the reaction.

The oxygen source used in the present invention may be high purity oxygen or molecular oxygen, air, or oxygen diluted with another gas which has no negative effects on the reaction, such as nitrogen, noble gases, argon, or carbon dioxide. The concentration of diluent gas, when present, in the oxygen source may amount to about 1 to about 95 volume %, preferably about 5 to about 90, and more preferably about 10 to about 80 volume %. In a preferred embodiment the oxygen source is molecular oxygen.

Oxygen in the form of an oxygen source may be introduced into the reaction mixture by any convenient means. In one embodiment the reaction mixture is agitated or stirred under a positive pressure of oxygen source. In a preferred embodiment oxygen source is introduced by sparging or bubbling into the reaction mixture at essentially atmospheric pressure.

The reaction mixture is heated to a temperature effective to promote oxidation of at least one methyl group of halo-ortho-xylene in the presence of the at least one catalyst and oxygen source. Preferably the reaction mixture is heated to a temperature in a range of between about 80° C. and the effective boiling point of the reaction mixture under the prevailing pressure. More preferably the reaction mixture is heated to a temperature in a range of between about 100° C. and about 230° C. and most preferably in a range of between about 150° C. and about 180° C. at atmospheric pressure.

Catalysts suitable for use in the present invention are typically poorly soluble in halo-ortho-xylene. However, as polar oxidation intermediates and products containing functionalities such as hydroxy, carboxaldehyde, or carboxylic acid are formed, the catalyst typically becomes increasingly soluble. For example, suitable catalysts may typically dissolve within about 0.5 to 1.0 hours at a temperature in a range of between about 100° C. and about 230° C., particularly at a temperature in a range of between about 150° C. and about 180° C.

The products of the oxidation reaction comprise those obtained by oxidation of at least one of and preferably both the two aromatic methyl groups. In particular the products comprise halotoluic acid and halophthalic anhydride, respectively. In a preferred embodiment the substrate halo-ortho-xylene comprises 4-chloro-ortho-xylene and the products comprise chlorotoluic acid and 4-chlorophthalic anhydride. In another preferred embodiment the substrate chloro-ortho-xylene comprises a mixture of 3-chloro- and 4-chloro-ortho-xylene and the products comprise chlorotoluic acids and a mixture of 3-chloro- and 4-chlorophthalic anhydride. When ortho-xylene is present in the substrate, then a small amount of phthalic anhydride and toluic acid may also be obtained in addition to the oxidation products of halo-ortho-xylene.

The product halophthalic anhydrides may be used in processes to make various types of aromatic polyethers, particularly polyetherimides. In one embodiment a product comprising 4-chlorophthalic anhydride (or a mixture thereof with 3-chlorophthalic anhydride) may be reacted with at least one diamine to prepare bis (chlorophthalimide) compounds which can serve as monomer for polyetherimide synthesis. For example, polyetherimides are conveniently prepared by the reaction of salts of dihydroxyaromatic compounds, such as bisphenol A disodium salt, with bis (halophthalimides) as illustrated by 1,3-bis[N-(4-chlorophthalimido)]benzene, which has the structure

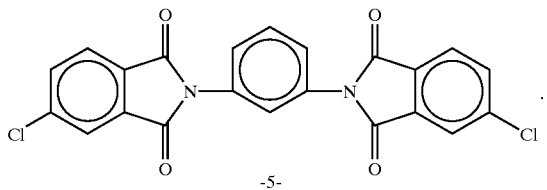

-5-

According to U.S. Pat. Nos. 5,229,482 and 5,830,974, the preparation of aromatic polyethers may be conducted in solution in relatively non-polar solvents, using a phase transfer catalyst which is substantially stable under the temperature conditions employed. Solvents disclosed in 5,229,482 include o-dichlorobenzene, dichlorotoluene, 1,2, 4-trichlorobenzene and diphenyl sulfone. In 5,830,974, monoalkoxybenzenes such as anisole, diphenylether, or phenetole are employed. Solvents of the same types may be used for the preparation of bis(halophthalimide) intermediates, particularly bis(chlorophthalimide) intermediates, for polyetherimides.

The reaction of diamine with 4-halophthalic anhydride (or a mixture thereof with 3-halophthalic anhydride) in the presence of any phthalic anhydride arising from ortho-xylene oxidation may produce trace amounts of the mono-halo species. For example the reaction of diamine with 4-chlorophthalic anhydride (or a mixture thereof with 3-chlorophthalic anhydride) in the presence of any phthalic anhydride arising from ortho-xylene oxidation may produce trace amounts of the mono-halo species, 1-N-(4-chlorophthalimido)-3-N-(phthalimido)benzene in addition to 1,3-bis[N-(4-chlorophthalimido)]benzene (optionally in the presence of 3-chloro species). The mono-halo species may serve as a chain-stopper in reaction with salts of dihydroxyaromatic compounds in polyetherimide synthesis.

The process of the present invention may be performed in batch mode or as a semi-continuous or continuous process. In one embodiment the products of the oxidation reaction may be isolated by conventional means, such as one or more steps of distillation or extraction. In another embodiment the products are at least partially recycled into a further oxidation process to increase conversion of halo-ortho-xylene or to increase conversion of halo-toluic acid, or both.

The invention is illustrated by the following examples. All parts and percentages are by weight.

EXAMPLE 1

In a 50 milliliter (ml) three-neck flask were placed 14.1 grams (g) of 4chloro-o-xylene and 0.249 g (1.00 millimole) of cobalt (II) acetate tetrahydrate. The mixture was magnetically stirred at 170° C. and oxygen gas was continuously bubbled through the mixture using a capillary inlet tube at a rate of 0.02 SCFH. In 112 hours of reaction the yield of 4-chlorophthalic anhydride was 8.3% and the yield of 4-chlorotoluic acid was 38.7%, both based on starting material.

EXAMPLES 2–7

The procedure of example 1 was repeated except that different catalysts and different reaction times were used. The catalysts used were manganese (II) acetate; a 1:1 (mole/mole) mixture of manganese (II) acetate and cobalt (II) acetate; vanadyl acetate; copper (I) acetate; molybdenyl (VI) acetylacetonate; or iron (II) acetate. Key products were 4-chlorophthalic anhydride (4-ClPA), chlorotoluic acid (CITAcid), and chlorotolualdehyde (CITAldehyde). The results are shown in Table 1.

| Example | Catalyst | Reaction time (hrs.) | Yield % | | |
|---|---|---|---|---|---|
| | | | 4-CIPA | CITAcid | CITAldehyde |
| 2 | Mn (II) acetate | 66 | 14.1 | 58.7 | 5.3 |
| 3 | Co (II) acetate + Mn (II) acetate (1:1) | 64 | 17.4 | 59.6 | 2.1 |
| 4 | Co (II) acetate + Mn (II) acetate (1.1) | 107 | 36.4 | 43.4 | 0.5 |
| 5 | Vanadyl (IV) acetate | 72 | 21.4 | 48.9 | 6.5 |
| 6 | Vanadyl (IV) acetate | 96 | 32.5 | 47.3 | 1.5 |
| 7 | Cu (I) acetate | 76 | 0.3 | 45.0 | 19.6 |
| 8 | Molybdenyl (VI) acetylacetonate | 111 | 8.7 | 30.0 | 10.0 |
| 9 | Fe (II) acetate | 70 | 12.3 | 32.2 | 22.1 |

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for oxidizing a substrate comprising at least one monohalo-ortho-xylene which comprises combining the substrate in the absence of solvent or added promoter with at least one metal catalyst and heating to a temperature in a range of between about 100° C. and about 230° C. in the presence of an oxygen source to produce a product mixture, wherein the substrate is oxidized in the liquid phase.

2. The method of claim 1 wherein the product mixture comprises a monohalo-phthalic anhydride and a monohalotoluic acid.

3. The method of claim 2 wherein the substrate comprises monochloro-ortho-xylene or monofluoro-ortho-xylene.

4. The method of claim 1 wherein the substrate further comprises at least one monohalo-toluic acid.

5. The method of claim 4 wherein the monohalo-toluic acid comprises at least one monochlorotoluic acid.

6. The method of claim 1 wherein the at least one metal catalyst is a metal compound with a metal selected from the group consisting of cobalt, manganese, vanadium, copper, molybdenum, and iron.

7. The method of claim 6 in which the molar ratio of halo-ortho-xylene substrate to the at least one metal catalyst is in a range of about 20–500:1.

8. The method of claim 1 in which the oxygen source is molecular oxygen.

9. The method of claim 1 in which the reaction mixture is heated to the temperature within the range at atmospheric pressure.

10. A method for oxidizing a substrate comprising 4-chloro-ortho-xylene which comprises combining the substrate in the absence of solvent or added promoter with at least one metal catalyst which is a metal compound with a metal selected from the group consisting of cobalt, manganese, vanadium, copper, molybdenum, and iron, and heating to a temperature in a range of between about 100° C. and about 230° C. in the presence of molecular oxygen to produce a product mixture comprising 4-chlorophthalic anhydride and monochlorotoluic acid, wherein the substrate is oxidized in the liquid phase.

11. The method of claim 10 wherein the substrate further comprises 3-chloro-ortho-xylene.

12. The method of claim 10 wherein the substrate further comprises monochlorotoluic acid.

13. The method of claim 10 wherein the substrate further comprises both 3-chloro-ortho-xylene and monochlorotoluic acid.

14. The method of claim 10 wherein the at least one metal catalyst is selected from the group consisting of acetate or acetylacetonate salts of cobalt (II), manganese (II), vanadium (IV), molybdenum (VI), and iron (II), and mixtures thereof.

15. The method of claim 14 in which the molar ratio of 4-chloro-ortho-xylene substrate to the at least one metal catalyst is in a range of about 80–180:1.

16. The method of claim 10 in which the reaction mixture is heated to the temperature within the range at atmospheric pressure.

17. A method for producing a product mixture comprising 4-chlorophthalic anhydride which comprises oxidizing a substrate comprising 4-chloro-ortho-xylene, optionally in the presence of monochlorotoluic acid, which comprises the steps of (i) combining substrate in the absence of solvent or added promoter with at least one metal catalyst which is a metal compound with a metal selected from the group consisting of cobalt, manganese, vanadium, copper, molybdenum, and iron, and heating in the presence of molecular oxygen to a temperature in a range of between about 100° C. and about 230° C. at atmospheric pressure, wherein the molar ratio of substrate to the at least one metal catalyst is in a range of about 80–180:1, and wherein the substrate is oxidized in the liquid phase; and (ii) isolating product comprising 4-chlorophthalic anhydride.

18. The method of claim 17 wherein the substrate further comprises 3-chloro-ortho-xylene.

* * * * *